(12) United States Patent
Shimazu et al.

(10) Patent No.: US 10,398,371 B2
(45) Date of Patent: Sep. 3, 2019

(54) PAIN MEASURING DEVICE

(71) Applicant: OSACHI CO., LTD., Okaya-shi, Nagano (JP)

(72) Inventors: Hideaki Shimazu, Tokyo (JP); Futoshi Shirakawa, Ootsuki (JP); Yasuyuki Yaguchi, Okaya (JP)

(73) Assignee: OSACHI CO., LTD., Okaya-Shi, Nagano (JP)

( * ) Notice: Subject to any disclaimer, the term of this patent is extended or adjusted under 35 U.S.C. 154(b) by 0 days.

(21) Appl. No.: 15/310,611

(22) PCT Filed: Mar. 29, 2016

(86) PCT No.: PCT/JP2016/060077
§ 371 (c)(1),
(2) Date: Nov. 11, 2016

(87) PCT Pub. No.: WO2017/056532
PCT Pub. Date: Apr. 6, 2017

(65) Prior Publication Data
US 2018/0192940 A1 Jul. 12, 2018

(30) Foreign Application Priority Data
Oct. 1, 2015 (JP) .................................. 2015-196228

(51) Int. Cl.
*A61B 5/00* (2006.01)
*A61B 10/00* (2006.01)
(Continued)

(52) U.S. Cl.
CPC ............ *A61B 5/4824* (2013.01); *A61B 10/00* (2013.01); *A61N 1/36021* (2013.01);
(Continued)

(58) Field of Classification Search
CPC ..... A61B 5/4824; A61B 5/1106; A61B 10/00; A61B 5/0478; A61B 5/053;
(Continued)

(56) References Cited

U.S. PATENT DOCUMENTS 5,806,522 A * 9/1998 Katims ................ A61B 5/4824
600/554
8,108,047 B2 * 1/2012 Schumann ........... A61H 39/002
607/46
(Continued)

FOREIGN PATENT DOCUMENTS

EP 1967135 A3 3/2009
JP 11146865 B 6/1999
(Continued)

OTHER PUBLICATIONS

Kim, Junho, et al. Correlations Between Electrically Quantified Pain Degree, Subjectively Assessed Visual Analogue Scale, and the McGill Pain Questionaire: A Pilot Study. Annals of Rehabilitation Medicine, vol. 38(5) (Oct. 30, 2014), pp. 665-672 [online], [retrieved on Aug. 23, 2018].*
(Continued)

Primary Examiner — Matthew Kremer
Assistant Examiner — Samuel C Kim
(74) Attorney, Agent, or Firm — Cantor Colburn LLP

(57) ABSTRACT

A problem to be solved is to use a measured pain degree for comparison with a pain degree of another subject or for diagnosis of a disease. A pain measuring device has an electrode to be attached to a subject and a stimulation current generation means generating a stimulation current to be supplied to the electrode. Then, the pain measuring device measures pain felt by the subject based on the stimulation current applied from the electrode to the subject. The pain measuring device has a means to display a relation between
(Continued)

a pain measurement value being a logarithmic value or a logarithmic-type value of a value founded on the stimulation current and a value of a VAS or a face scale which the subject selects.

2 Claims, 10 Drawing Sheets

(51) Int. Cl.
| | |
|---|---|
| *G16H 40/63* | (2018.01) |
| *G16H 50/20* | (2018.01) |
| *A61N 1/36* | (2006.01) |
| *G06F 19/00* | (2018.01) |
| *A61B 5/0478* | (2006.01) |
| *A61B 5/053* | (2006.01) |

(52) U.S. Cl.
CPC ............. *G06F 19/00* (2013.01); *G16H 40/63* (2018.01); *G16H 50/20* (2018.01); *A61B 5/0478* (2013.01); *A61B 5/053* (2013.01); *A61N 1/36014* (2013.01)

(58) Field of Classification Search
CPC ............ A61N 1/36021; A61N 1/36014; G06F 19/00; G16H 50/20; G16H 40/63
See application file for complete search history.

(56) References Cited

U.S. PATENT DOCUMENTS

| | | | |
|---|---|---|---|
| 2002/0058867 A1* | 5/2002 | Breiter | ................ A61B 5/0484 600/407 |
| 2005/0154329 A1 | 7/2005 | Shimazu et al. | |
| 2017/0065229 A1* | 3/2017 | Howard | ............... A61B 5/7267 |

FOREIGN PATENT DOCUMENTS

| | | |
|---|---|---|
| JP | 2005176937 A | 7/2005 |
| JP | 2007130034 B | 5/2007 |
| WO | 2008129702 A1 | 10/2008 |

OTHER PUBLICATIONS

Extended European Search Report corresponding to Application No. 16791290.6-1126/3175796 PCT/JP2016060077; dated Feb. 8, 2018.

Junho Kim et al., "Correlations Between Electrically Quantified Pain Degree, Subjectively Assessed Visual Analogue Scale, and the McGill Pain Questionnaire: A Pilot Study," Annals of Rehabilitation Medicine; vol. 38, No. 5, Oct. 30, 2014, pp. 665-672.

* cited by examiner

PAIN MEASURING DEVICE

FIELD

This is the U.S. national stage of application No. PCT/JP2016/060077, filed on Mar. 29, 2016. Priority under 35 U.S.C. § 119(a) and 35 U.S.C. § 365(b) is claimed from Japanese Application No. 2015-196228, filed Oct. 1, 2015, the disclosure of which is also incorporated herein by reference.

TECHNICAL FIELD

The present invention relates to a pain measuring device.

BACKGROUND ART

A pain measuring device for objectively measuring pain felt by a subject is suggested by the present applicant (for example, see Patent Literature 1). The pain measuring device disclosed in Patent Literature 1 has a configuration where an electrode is attached to the subject and a degree of the pain felt by the subject can be evaluated quantitatively based on a stimulation current applied from the electrode to the subject. That is, the pain measuring device disclosed in Patent Literature 1 has a configuration where the degree of the pain felt by the subject can be evaluated quantitatively by measuring largeness (current value of the stimulation current) of electric stimulation which is felt to be nearly equal to intensity of the pain felt by the subject. Further, in this pain measuring device, a stimulation current which has a frequency characteristic that the subject does not feel pain is used as the stimulation current applied to the subject.

CITATION LIST

Patent Literature

{PTL 1} JP 3808492 A

SUMMARY OF INVENTION

Technical Problem

Though the aforementioned pain measuring device has the configuration where the degree of the pain felt by the subject can be evaluated quantitatively, the measured largeness of the pain is merely digitized and displayed as a unique pain index which the apparatus has. That apparatus is only used for comparison with a record of the degree of pain of the past for one subject, and cannot be used for comparison with a pain degree of another subject or for diagnosis of a disease.

The present invention is made under these circumstances, and its object is to provide an apparatus enabling either one of the following two. The one is to provide a pain measuring device which enables a measured pain degree to be used for comparison with a pain degree of another subject. The other is to provide a pain measuring device which enables a measured pain degree to be used for diagnosis of a disease.

Solution to Problem

The present invention is a pain measuring device which includes an electrode to be attached to a subject and a stimulation current generation means generating a stimulation current to be supplied to the electrode and which measures pain felt by the subject based on the stimulation current applied from the electrode to the subject, and the pain measuring device for a human body has a means to display a relationship between a pain measurement value being a logarithmic value of a value founded on the stimulation current and a value of a VAS (visual analogue scale) or a face scale which the subject selects.

The present invention is a pain measuring device which includes an electrode to be attached to a subject and a stimulation current generation means generating a stimulation current to be supplied to the electrode and which measures pain felt by the subject based on the stimulation current applied from the electrode to the subject, and the pain measuring device for a human body has a means to display a relationship between a logarithmic value of a pain equivalent current value being a value of the stimulation current equivalent to pain felt by the subject and a value of a VAS or a face scale which the subject selects.

In the aforementioned pain measuring device, the means to display can display the measurement value of the measured pain or the pain equivalent current value in the logarithmic format.

The aforementioned pain measuring device can have: a means to compare a relationship between the measurement value of the measured pain or the pain equivalent current value and the value of the VAS or the face scale in a chronological order; and a means to classify factors of the pain of the subject or to identify a cause of the pain in correspondence with a result of the comparison. At this time, the means to classify the factors of the pain or to identify the cause of the pain has any one or two or more of nociceptive pain, psychogenic pain and neuropathic pain as a classification or identification target.

Advantageous Effects of Invention

According to the present invention, a measured pain degree can be used for comparison with a pain degree of another subject or for diagnosis of a disease.

BRIEF DESCRIPTION OF DRAWINGS

FIG. 10(A) shows the measurement result at a time that the stimulation current according to the embodiment of the present invention is applied to the subject, while FIG. 10(B) shows the measurement result at a time that the stimulation current constituted by a conventional rectangular wave is applied to the subject.

DESCRIPTION OF EMBODIMENTS

Hereinafter, a best mode for carrying out the present invention will be described based on the drawings.

(Schematic Configuration of Pain Measuring Device)

Figure 1:
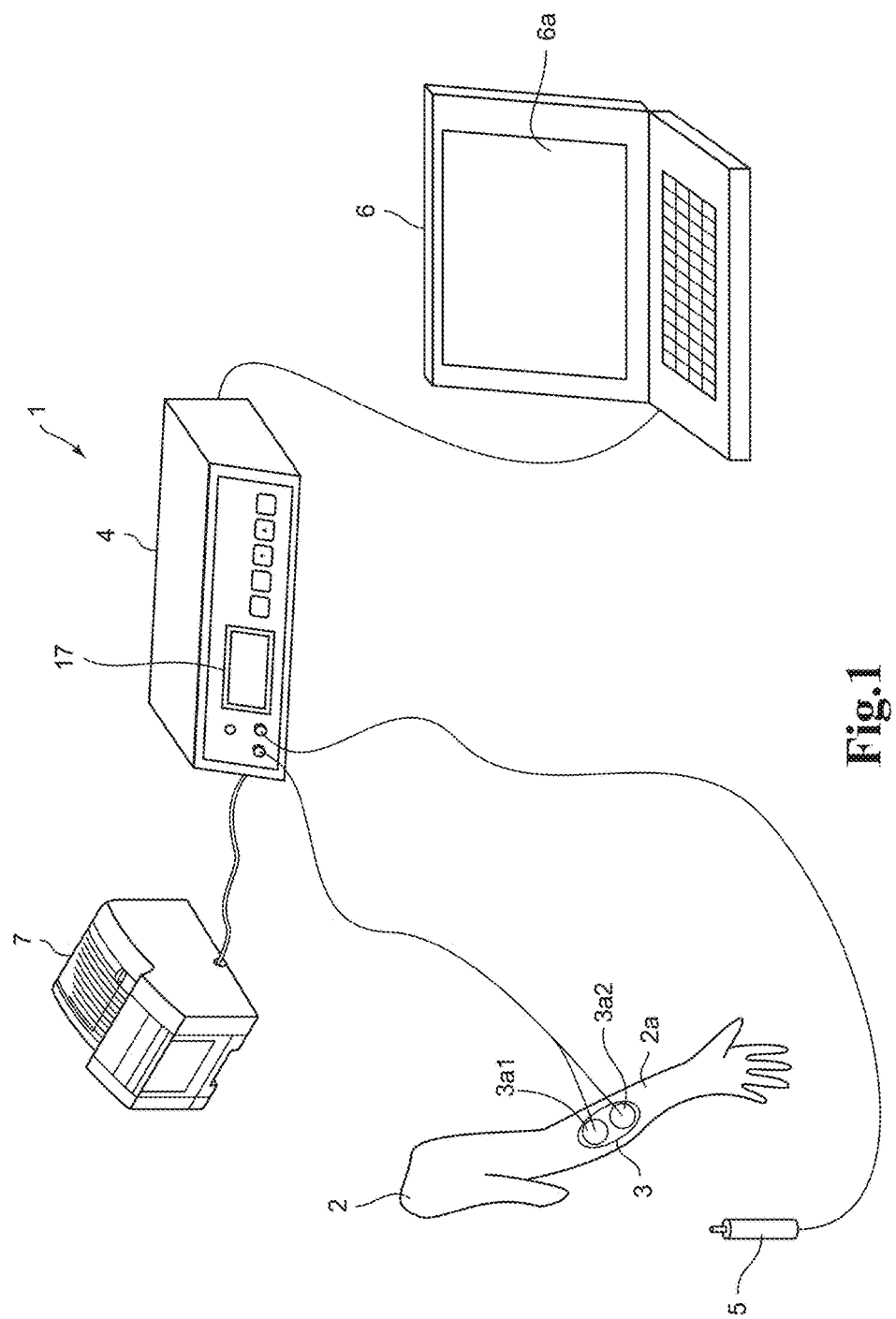
FIG. 1 is a perspective view showing a configuration of a pain measuring device according to an embodiment 1 of the present invention.
Figure 2:
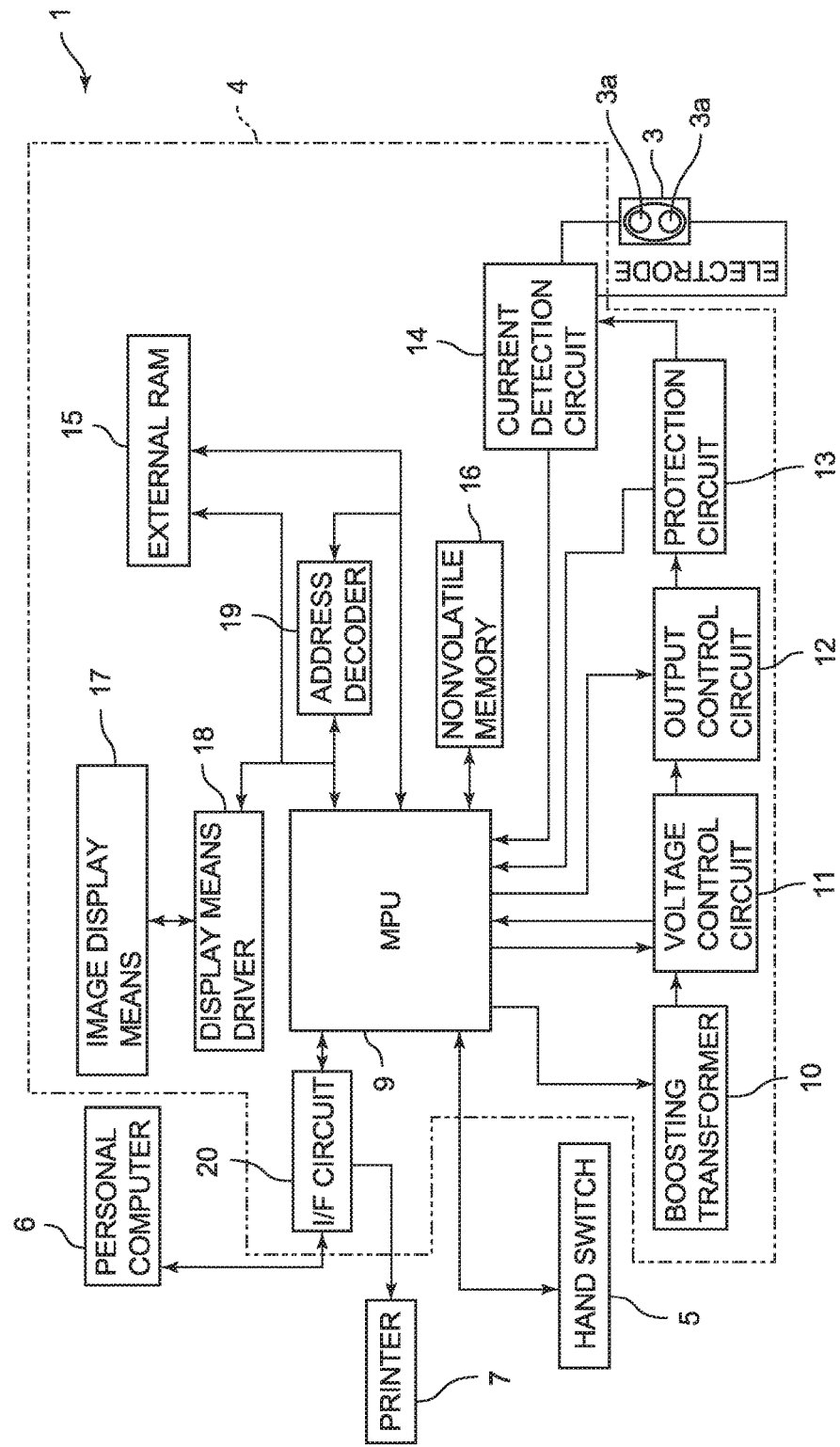
FIG. 2 is a block diagram showing a schematic configuration of a main body unit of the pain measuring device shown in FIG. 1 and peripheral devices thereof.
Figure 3:
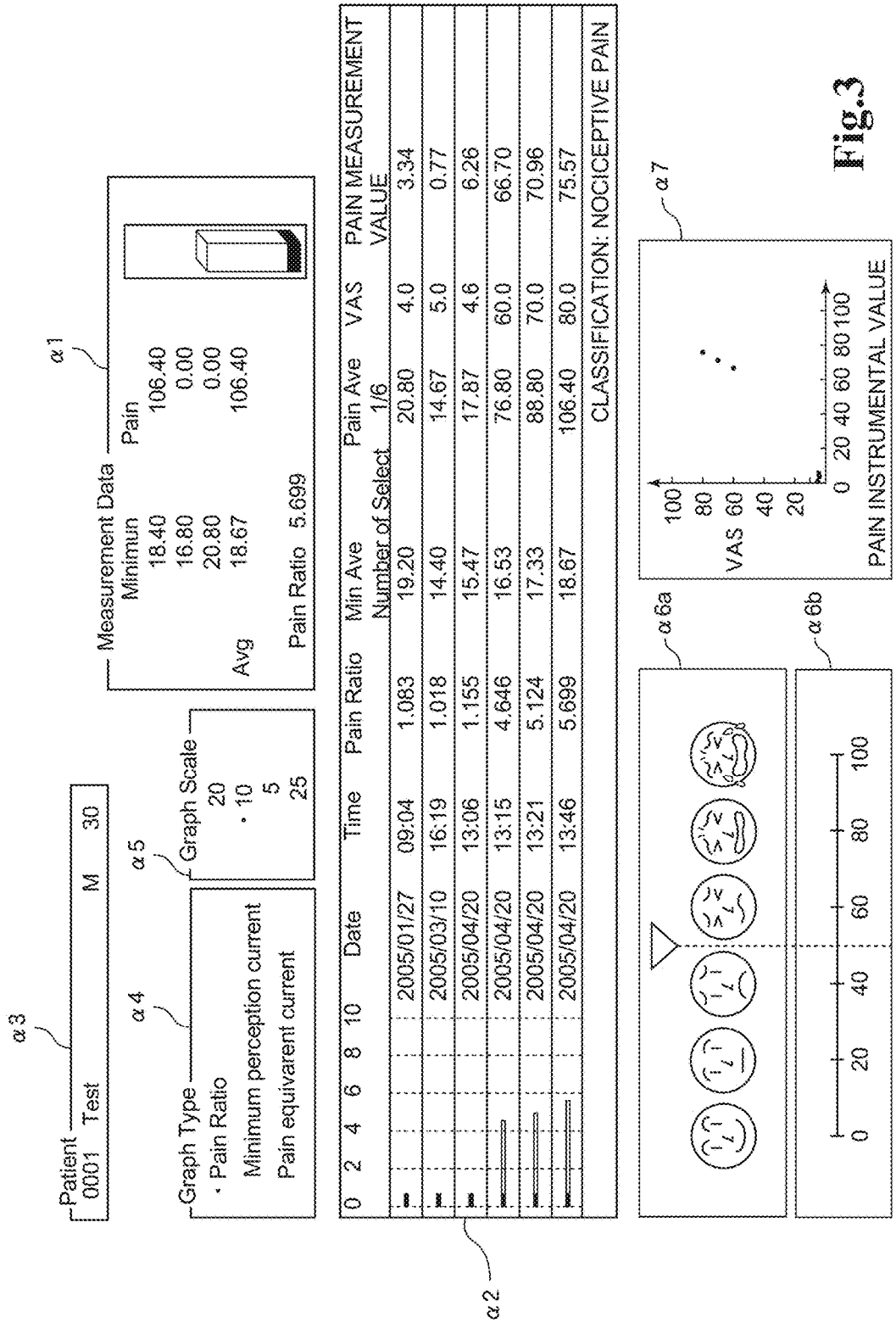
FIG. 3 is a diagram showing an example of screen display of a personal computer shown in FIG. 1.

FIG. 1 is a perspective view showing a configuration of a pain measuring device 1 according to an embodiment 1 of the present invention. FIG. 2 is a block diagram showing a schematic configuration of a main body unit 4 of the pain measuring device 1 shown in FIG. 1 and peripheral devices thereof. FIG. 3 is a diagram showing an example of screen display of a personal computer 6 shown in FIG. 1.

The pain measuring device 1 according to the present embodiment is an apparatus for objectively measuring pain felt by a subject 2 due to a disease or an injury. In other words, the pain measuring device 1 of the present embodiment is a device for quantitatively evaluating the pain felt by the subject 2. This pain measuring device 1 has, as shown in FIG. 1, an electrode band 3 which is attached to an inside of an upper arm 2a of the subject 2, the main body unit 4 which supplies a predetermined stimulation current to the electrode band 3, a hand switch 5 which the subject 2 operates at a time of measuring pain, the personal computer (PC) 6 which outputs a predetermined operation signal to the main body unit 4 and displays a measurement result of pain, and a printer 7 which prints and outputs the measurement result of pain on printing paper or the like. The electrode band 3, the hand switch 5, the PC 6 and the printer 7 are connected to the main body unit 4 by a predetermined cable. Note that the PC 6 may not be connected.

In the present embodiment, though the electrode band 3 is attached to the inside of the upper arm 2a of the subject 2, a fixing point of the electrode band 3 may be a place other than the inside of the upper arm 2a as long as muscle masses and sweat glands are few and easy attachment is available in that place. For example, the fixing point of the electrode band 3 may be a heel. By attaching the electrode band 3 to the place where the muscle masses are few as described above, it is possible to prevent intermittent or continuous contraction of muscle. The electrode band 3 is provided with two electrodes 3a1, 3a2 and the simulation current is supplied to the electrode 3a1, 3a2.

The main body unit 4 has, as shown in FIG. 2, a micro processing unit (MPU) 9, a boosting transformer 10, a voltage control circuit 11, an output control circuit 12, a protection circuit 13, a current detection circuit 14, an external random access memory (RAM) 15, a nonvolatile memory 16, an image display means 17, a display means driver 18, an address decoder 19, and an I/F (interface) circuit 20.

The MPU 9 has a read only memory (ROM), a random access memory (RAM), a timer, and an output interface, which are not illustrated, in its inside. When an operation signal is inputted from the PC 6 to the MPU 9 via the I/F/ circuit 20, the MPU 9 processes the operation signal from the PC 6 in accordance with the program stored in the ROM inside thereof while using a temporary storage function of the external RAM 15, and executes a predetermined algorithm. Further, by executing the predetermined algorithm, the MPU 9 supplies drive signals to the boosting transformer 10, the voltage control circuit 11, and the output control circuit 12, respectively.

The boosting transformer 10 boosts a voltage from a not-shown direct-current power supply in response to the drive signal from the MPU 9. More concretely, the boosting transformer 10 drives a transistor based on the square-wave shaped drive signal from the MPU 9 using a timer, to boost the voltage from the direct current power supply. For example, the boosting transformer 10 boosts a voltage of 12V applied by the direct-current power supply to 100 V to 120 V. The voltage control circuit 11 adjusts a direct-current voltage output outputted from the boosting transformer 10 in response to the drive signal from the MPU 9. Further, as shown in FIG. 2, a detection signal for detecting a voltage value in the voltage control circuit 11 is outputted from the voltage control circuit 11 and inputted to the MPU 9. Based on the detection signal inputted to the MPU 9, control is carried out so that a voltage equal to or more than a prescribed value may not be outputted from the output control circuit 12.

The output control circuit 12 is a pulse width modulation (PWM) control circuit for controlling a rectified voltage outputted from the voltage control circuit 11 by PWM. This output control circuit 12, for example, outputs a pulsed voltage in a range of 5 V to 100 V in response to the drive signal from the MPU 9. The protection circuit 13 is a limiter circuit which prevents a current equal to or larger than a predetermined value from being supplied to the electrode 3a attached to the subject 2 from the output control circuit 12. As shown in FIG. 2, the detection signal for detecting a current limit value is outputted from the protection circuit 13 and inputted to the MPU 9.

The current detection circuit 14 is a circuit for detecting an effective value of a current applied from the protection circuit 13 to the subject 2 via the electrode 3a. The current detection circuit 14 of the present embodiment is constituted, for example, by a resistor or an operational amplifier. As shown in FIG. 2, the detection signal for detecting the current value of the stimulation current (that is, the stimulation current applied to the subject 2) supplied to the electrode 3a is outputted from the current detection circuit 14 and inputted to the MPU 9. In the present embodiment, a waveform of the stimulation current (that is, the stimulation current applied to the subject 2) supplied from the output control circuit 12 to the electrode 3a is a pulse waveform of 50 Hz cycle.

As described above, in the present embodiment, a stimulation current generation means which generates the stimulation current supplied to the electrode 3a is constituted by the MPU 9, the direct-current power supply (not shown), the boosting transformer 10, the voltage control circuit 11, the output control circuit 12, the protection circuit 13, and the current detection circuit 14.

The external RAM 15 is a memory for the MPU 9 to execute the predetermined algorithm, as described above. This external RAM 15 is not required to be provided if a capacity of the RAM inside the MPU 9 is sufficient. The nonvolatile memory 16 is a memory which stores a rise speed (that is, an increase degree of the stimulation current supplied to the electrode 3a) of a voltage outputted from the output control circuit 12, a predetermined set value such as a limit value or the like the limit value of the voltage supplied to the current detection circuit 14, or measurement data of pain of past predetermined number of times.

The image display means 17 is a display device such as a liquid crystal display device which displays the voltage value in the voltage control circuit 11 and the current value of the stimulation current supplied to the electrode 3a to the outside of the main body unit 4 (see FIG. 1). This image display means 17 displays image data outputted from the MPU 9 and processed in the display means driver 18.

The address decoder 19 is a logic circuit for exchanging signals between the external RAM 15 or the display means driver 18 and the MPU 9. Further, the I/F circuit 20 is a circuit for exchanging signals between the MPU 9 and the PC 6 and for supplying a signal from the MPU 9 to the printer 7.

The hand switch 5 is for the subject 2 to halt supply of the stimulation current to the electrode 3a and to start supply of the stimulation current. Further, the PC 6 has a display unit 6a for displaying a measurement result of pain in the pain measuring device 1, as shown in FIG. 1. This display unit 6a is, for example, a liquid crystal display device. Further, in the display unit 6a, for example, the measurement result in the pain measuring device 1 is displayed as FIG. 3. Display contents of the display unit 6a shown in FIG. 3 will be described later.

(Characteristic of Stimulation Current)

Figure 4:
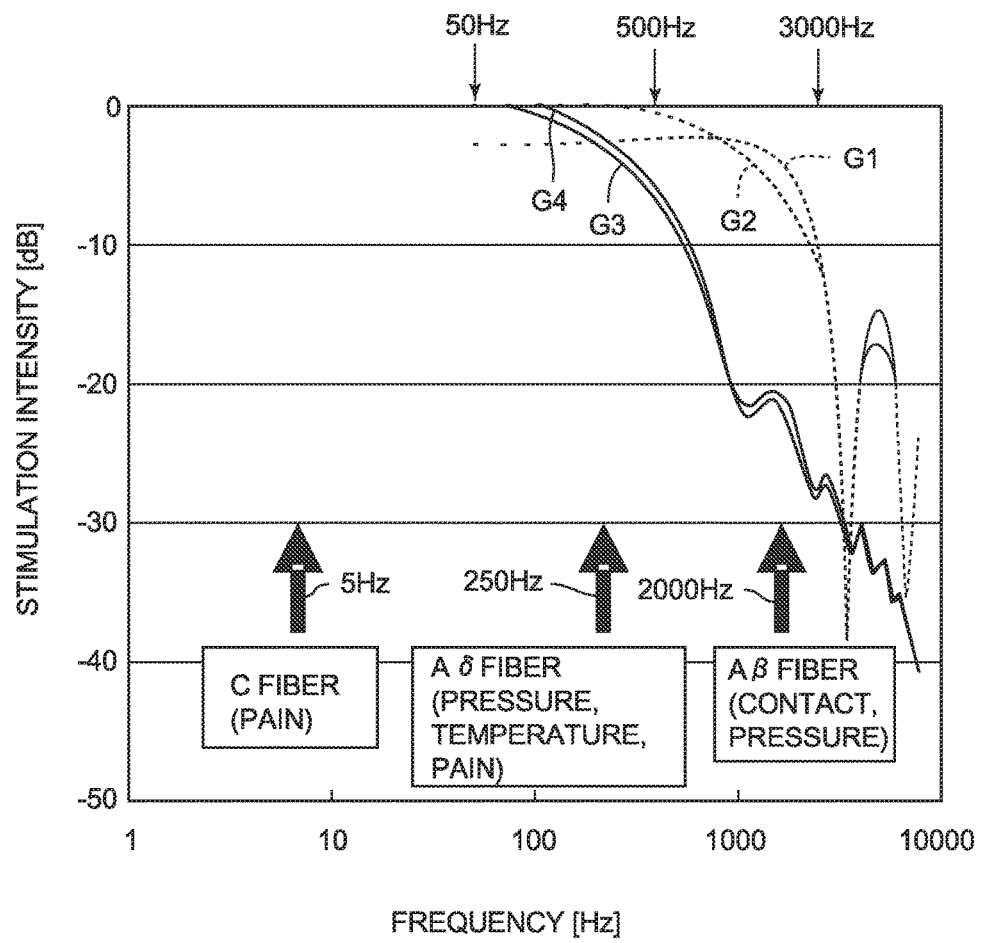
FIG. 4 is a graph showing peak values of power spectra indicating intensity of stimulation per each frequency component of stimulation currents applied from an electrode shown in FIG. 1 to a subject.
Figure 5:
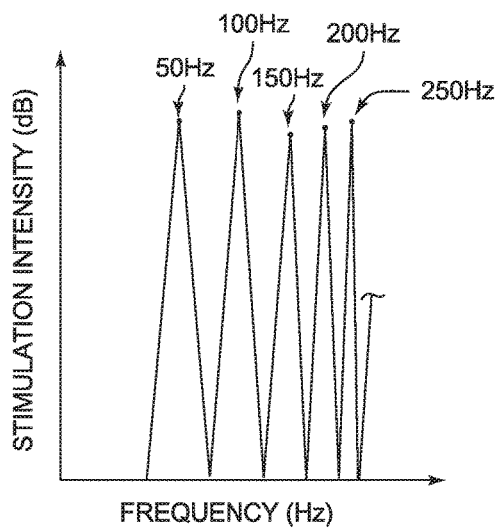
FIG. 5 is a graph for explaining actual change of the power spectrum indicating intensity of stimulation per each frequency component of the stimulation current applied from the electrode shown in FIG. 1 to the subject.

FIG. 4 is a graph showing peak values of power spectra indicating intensity of stimulation per each frequency component of stimulation currents applied to the subject 2 from the electrode 3a shown in FIG. 1. FIG. 5 is a graph for explaining actual change of the power spectrum indicating the intensity of simulation per each frequency component of the stimulation current applied from the electrode 3a shown in FIG. 1 to the subject 2.

The present applicant has been long studied what kind of stimulation current enables measurement of a degree of pain felt by the subject 2 in a broad range by electric stimulation without pain. As a result of that study, it is found that the stimulation current enabling measurement of the degree of the pain felt by the subject 2 accurately in the broad range by electric stimulation without pain has a certain characteristic. Then, the present applicant makes the pain measuring device 1 of the present embodiment generate the stimulation current having that specific property. Hereinafter, there will be described the characteristic of the stimulation current (that is, the stimulation current applied from the electrode 3a to the subject 2 in the present embodiment) which enables measurement of the degree of the pain felt by the subject 2 accurately in the broad range by the electric stimulation without pain.

A particular pattern is exhibited by a power spectrum indicating intensity of stimulation per each frequency component of the simulation current (that it, a stimulation current of the present embodiment) which enables measurement of the degree of the pain felt by the subject 2 in the broad range by the electric stimulation without pain, that is, concretely, the power spectrum indicating the intensity of the stimulation per each frequency component of a pulse wave of the stimulation current, the particular pattern having a peak value at every frequency of integral multiple of 50 Hz and does not have a peak value at a frequency other than the above. In other words, as schematically shown in FIG. 5, the power spectrum of the stimulation current in the present embodiment has the peak value at every 50 Hz, that is, at 50 Hz, 100 Hz, 150 Hz, and so on, and does not have the peak value at the frequency other than the above. Note that the power spectrum of the stimulation current increases/decreases depending on each frequency as shown in FIG. 5.

In FIG. 4, only the peak values of the power spectra of the stimulation currents of the present embodiment are indicated by dots (see graphs G1, G2). Further, in FIG. 4, as a reference, there are indicated only peak values of power spectra of stimulation currents (hereinafter, referred to as conventional stimulation currents) constituted by rectangular pulse waves which the present applicant has conventionally used for a pain measuring device (see graphs G3, G4). Here, a pulse wave of 50 Hz cycle is used as the pulse wave of the conventional stimulation current. As a result of the study of the present applicant, it is found that the power spectrum of the conventional stimulation current also exhibits a particular pattern which has the peak value at every frequency of integral multiple of 50 Hz and does not have the peak value at a frequency other than the above similarly to the power spectrum of the stimulation current of the present embodiment, by coincidence. In FIG. 4, in order to differentiate from the peak value of the power spectrum of the stimulation current of the present embodiment, there is illustrated a state where the peak values of the power spectrum of the conventional stimulation current are connected by solid lines. In FIG. 4, a horizontal axis indicates a frequency (unit: Hz) and a vertical axis indicates intensity (unit: dB (decibel)) of the stimulation. Further, FIG. 4 is a double-logarithmic graph in which in addition to the vertical axis the horizontal axis also has a logarithmic scale.

The current values of the stimulation current of the present embodiment and the conventional stimulation current which have the peak values of the power spectra shown in FIG. 4 are equal. Further, in proportion to increase/decrease of the current value of each stimulation current, each peak value (that is, intensity of stimulation per each frequency component) of the power spectra shown in FIG. 4 increases and decreases.

In FIG. 4, as graphs indicating transition of the peak values of the power spectra of the stimulation currents of the present embodiment, two graphs of the graphs G1 and the graph G2 are shown. A difference between the graph G1 and the graph G2 occurs due to variation or the like variation of the stimulation current at a measurement time. Similarly, in FIG. 4, as graphs indicating transition of the peak values of the power spectra of the conventional stimulation currents, two graphs of the graph G3 and the graph G4 are shown, and a difference between the graph G3 and the graph G4 also occurs due to variation or the like variation of the stimulation current at a measurement time.

As is known from FIG. 4, patterns of change largely differ between the graphs G1, G2 and the graphs G3, G4. As is known from the graphs G1, G2, the peak values of the power spectra of the stimulation currents of the present embodiment are almost equal in a range of 50 Hz to 500 Hz. In particular, in the graph G1, the peak values of the power spectrum of the stimulation current of the present embodiment are almost equal in a range of 50 Hz to 1050 Hz. Further, the peak values of the power spectra of the stimulation currents of the present embodiment are largest in a range of 50 Hz to 2000 Hz. More concretely, in the graph G1, the peak values of the power spectrum around 1050 Hz are largest and in the graph G2, the peak values of the power spectrum around 150 Hz are largest. In contrast, as is known from the graphs G3, G4, the peak values of the power spectra of the conventional stimulation currents decrease at frequencies equal to or more than 100 Hz. In particular, the peak values decrease rapidly at frequencies equal to or more than 500 Hz.

In a case where a stimulation current (a stimulation current having only a constant frequency component) of a simple sine wave is applied to the subject 2, as shown in FIG. 4, it has been conventionally known that what stimulates an Aδ fiber related to transmission of momentary keen pain, a pressure or a temperature efficiently is a stimulation current having a 250 Hz frequency component and that what stimulates an Aβ fiber which is related to transmission of contact and a pressure and is not related to transmission of pain efficiently is a stimulation current having a 2000 Hz frequency component. Further, in a case where the stimulation current of the simple sine wave is applied to the subject 2, it has been conventionally known that what stimulates a *C fiber* which is related to transmission of continuous dull pain efficiently is a stimulation current having a 5 Hz frequency component.

The stimulation current of the present embodiment and the conventional stimulation current contain the 250 Hz frequency component which stimulates the Aδ fiber efficiently and the 2000 Hz frequency component which stimulates the Aβ fiber efficiently. Further, the stimulation current of the present embodiment and the conventional stimulation current do not contain the 5 Hz frequency component which stimulates the C fiber efficiently at all or include slight (for example, equal to or less than one thousandth of the 250 Hz or 2000 Hz frequency component) 5 Hz frequency component which can be ignored compared with the 250 Hz or 2000 Hz frequency component.

Note that what relates to stimulation to the Aδ fiber is considered to be an integration value of 50 Hz to 500 Hz of the power spectrum of the stimulation current, and what relates to stimulation to the Aβ fiber is considered to be an integration value of 50 Hz to 3000 Hz of the power spectrum of the stimulation current.

(Measurement Method of Pain)

Figure 6:
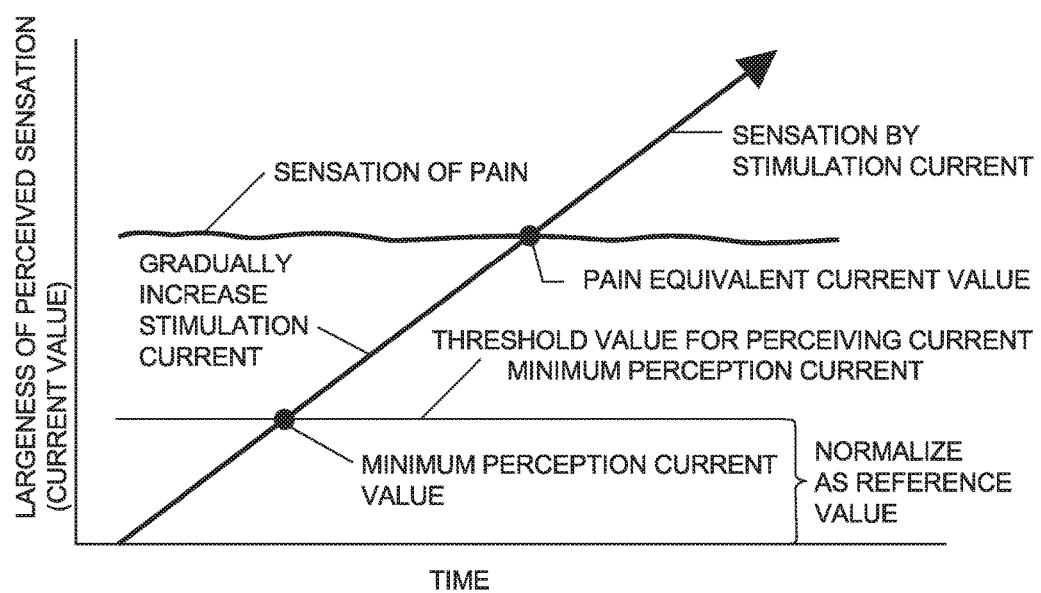
FIG. 6 is a graph for explaining a concept of a measurement method of pain by the pain measuring device shown in FIG. 1.
Figure 7:
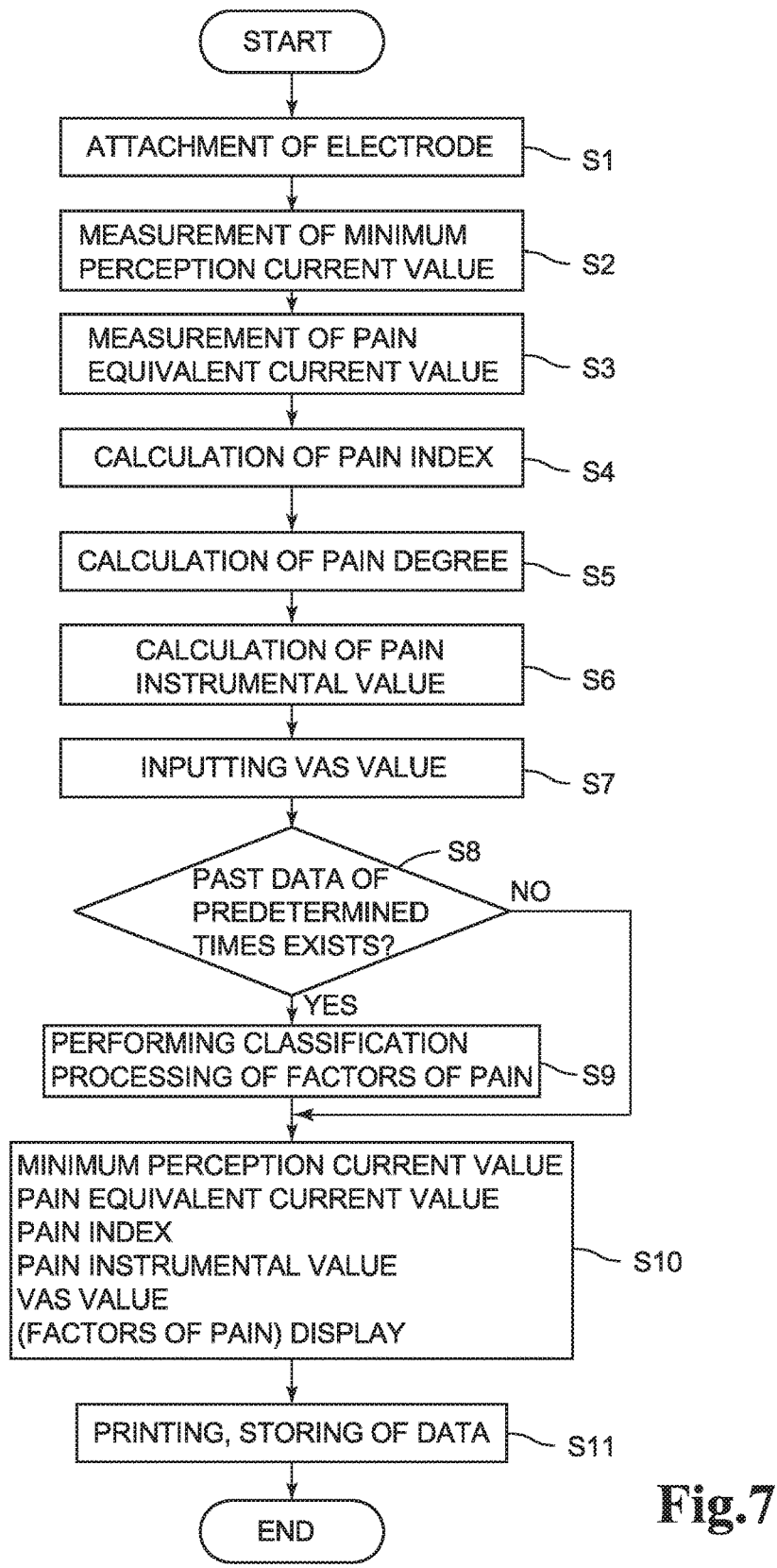
FIG. 7 is a flowchart showing a pain measurement procedure by the pain measuring device shown in FIG. 1.

FIG. 6 is a graph for explaining a concept of a measurement method of pain by the pain measuring device 1 shown in FIG. 1. FIG. 7 is a flowchart showing a pain measurement procedure by the pain measuring device 1 shown in FIG. 1.

Hereinafter, the measurement method of pain by the pain measuring device 1 will be described.

In the present embodiment, in order to measure pain felt by the subject 2 (that is, in order to evaluate pain quantitatively), two current values of a stimulation current different in largeness are measured. As shown in FIG. 6, one is the current value (that is, a perception threshold value. Hereinafter, this current value is referred to as a "minimum perception current value") of the stimulation current at a time that the subject 2 feels electric stimulation first when the current value of the stimulation current applied to the subject 2 is gradually increased from "0", and the other is the current value (hereinafter, this current value is referred to as a "pain equivalent current value") of the stimulation current which gives a sensation nearly equal to a sensation of pain felt by the subject 2 due to a disease or the like when the current value of the stimulation current is further increased.

The minimum perception current value is a reference value for evaluating pain quantitatively. In other words, a value obtained by dividing the pain equivalent current value by the minimum perception current value is defined as a pain index, and the pain felt by the subject 2 is evaluated quantitatively by this pain index. Even if factors of pain are the same, perception of the pain is different depending on persons, and thus evaluating the pain by the pain index enables quantitative evaluation of pain in which influence of differences of perception of the pain between individuals is suppressed.

Further, in the present embodiment, the pain felt by the subject 2 is evaluated by a pain measurement value calculated from a pain degree defined by a formula below, and factors of the pain are classified or a cause of the pain is identified based on a correspondence between the pain measurement value and the VAS. Here, a role of the pain measurement value is, by making a numerical value of the pain degree in a range of 0 to 100, to adapt to a value of the VAS which also corresponds to 0 to 100. Further, the pain measurement value is for making an extreme fluctuation of a numerical value hard to occur when the minimum perception current value rises due to medication or the like medication of a pain relief product. Note that as the values of the VAS, values from 0 to 10 or 0 to 20 may be adopted, but, here, values from 0 to 100 are adopted.

The pain index is defined as (pain index)=(pain equivalent current value)/(minimum perception current value).

Subsequently, the pain degree is defined as (pain degree)=((pain equivalent current value)−(minimum perception current value)/(minimum perception current value))×100.

To a formula 1 of the pain measurement value using the pain degree, either one of two formulas below is applied.

(first pain measurement value)=$Log_e$ 29.046 (pain degree)−111.6

(first pain measurement value)=$Log_e$ 38 ((pain degree)+100)−175

Otherwise, to a second pain measurement value using the pain index, a formula below is applied.

(second pain measurement value)=100×$Log_{10}$ (pain index)

Otherwise, as a third pain measurement value, a formula shown below may be applied. According to the formula below, it is possible to calculate a logarithmic value though a logarithm is not used.

(third pain measurement value)=(((pain index)−1)/(pain index))×100

The pain measurement procedure by the pain measuring device 1 is, for example, as expressed by a flowchart shown in FIG. 7. In other words, in measuring the pain felt by the subject 2, first, the electrode pad 3 is attached to the subject 2 (step S1). Thereafter, the current value of the stimulation current applied to the subject 2 is gradually increased from 0. Then, when perceiving electric stimulation first, the subject 2 presses a switch of the hand switch 5 held in a hand. As a result that the switch of the hand switch 5 is pressed, the stimulation current is stopped, and a current value at that time is stored in the external RAM 15 or nonvolatile memory 16 as a minimum perception current value (step S2). Note that it is also possible that the stimulation current is not stopped and only that value is stored in the external RAM 15 or nonvolatile memory 16.

Thereafter, the current value of the stimulation current is further increased, and when perceiving a different kind of electric stimulation (electric stimulation without pain) which is felt to have intensity nearly equal to that of a sensation of the pain felt by the subject 2, the subject 2 presses the switch of the hand switch 5 held in the hand. As a result that the switch of the hand switch 5 is pressed, the stimulation current is halted and a current value at that time is stored in the external RAM 15 or nonvolatile memory 16 as a pain equivalent current value (step S3). In the MPU 9, by dividing the stored pain equivalent current value by the minimum perception current value which is also stored, a pain index is calculated (step S4). Subsequently, the MPU 9 calculates a pain degree based on the above-described calculation formula of the pain degree (step S5). Further, the MPU 9 calculates a first pain measurement value based on the above-described calculation formula 1 of the first pain measurement value (step S6). Other than the above, the pain index may be calculated based on the above-described pain index calculation formula instead of the above-described pain degree calculation formula (step S4), whereby the second or the third pain measurement value is calculated from the calculated pain index (step S6).

Figure 8:
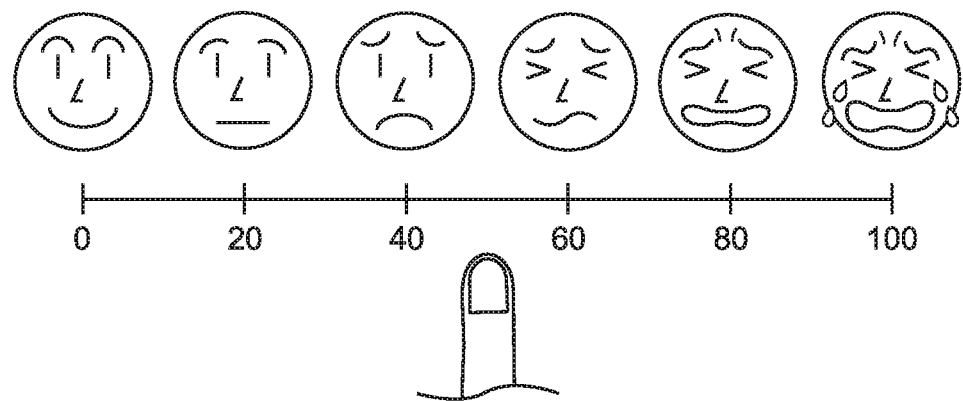
FIG. 8 is a diagram for explaining a method where the subject selects a VAS.

Thereafter, the value of the VAS which corresponds to the sensation of the pain felt by the subject 2 is inputted and stored in the external RAM 15 or nonvolatile memory 16 (step S7). As a method for the subject 2 to select the value of the VAS, as shown in FIG. 8, a sheet on which numerical values of the VAS or a face scale are (is) printed or a screen on which the numerical values of the VAS or the face scale are (is) displayed is shown to the subject 2, and selection is carried out as a result that the subject 2 himself/herself points to the numerical value of the VAS or the face scale corresponding to the pain felt by the subject 2. Note that the numerical values of the VAS or the face scale may be displayed in the display unit 6a of the PC 6. Further, a step of inputting the value of the VAS is explained as the step S7 in an example of FIG. 7, but inputting of the value of the VAS may be carried out at any timing from the start to the end of the flowchart shown in FIG. 7, as long as the selection of the value of the VAS by the subject 2 is finished.

Next, if past data of a predetermined number of times exists with regard to the value of the VAS and data of the pain measurement value (Yes in a step S8), the MPU 9 carries out a classification process of factors of the pain (step S9). On the other hand, if past data of the predetermined number times is absent with regard to the value of the VAS and data of the pain measurement value (No in the step S8), the process is proceeded to a step S10.

In the step S10, there are displayed, in the display unit 6a of the PC 6, the minimum perception current value measured in the step S2, the pain equivalent current value measured in the step S3, the pain index calculated in the step S4, the pain measurement value calculated in the step S6, the VAS value inputted in the step S7, and a result of classification of the factors of pain which is carried out in the step S9 in a case of Yes in the step S8. Further, the various measurement results describe above are printed on printing paper by the printer 7 or data of the measurement results is stored in the PC 6 (step S11), and the measurement of pain ends.

The classification process of factors of pain in the step S9 will be described with reference to FIG. 9. Note that this process is also a process to identify the cause of pain. The factors of pain are classified largely into (1) nociceptive pain, (2) psychogenic pain, and (3) neuropathic pain. The nociceptive pain is acute pain caused as a result that a nociceptor which feels pain is stimulated. The psychogenic pain is pain influenced by a psychological factor. The neuropathic pain is chronic pain due to a failure or the like failure of a peripheral nerve or a central nerve.

Figure 9:
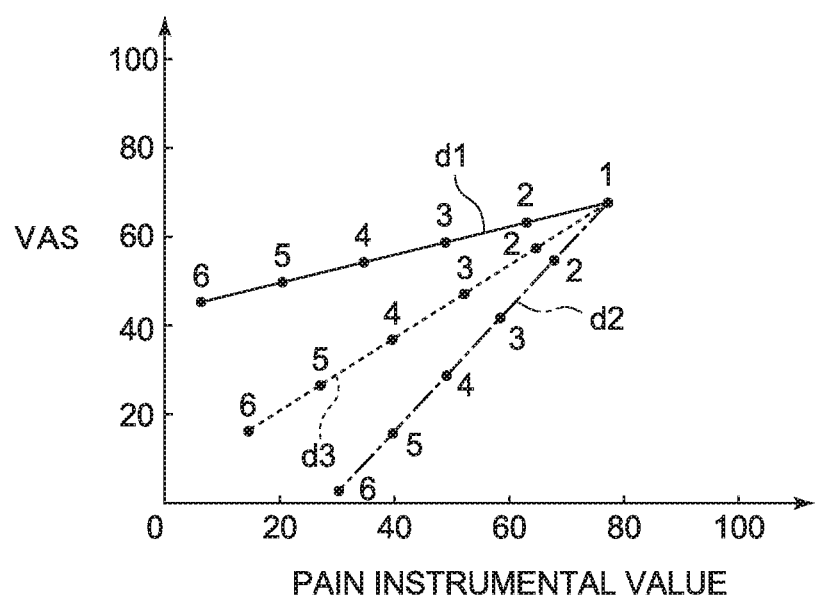
FIG. 9 is a diagram showing a correspondence between the VAS and a pain measurement value.

In an example of FIG. 9, measurement data of pain of past six times is stored in the nonvolatile memory 16. For example, in a case where the measurement data of pain of past six times is in a situation as a progress d1 indicated by a solid line in FIG. 9, a decrease of the value of the VAS in a vertical axis which is regarded as subjective is smaller compared with a decrease of the pain measurement value in a horizontal axis which is regarded as objective data. Based on the above, it is understood that decrease of the pain felt by the subject 2 is small in comparison with decrease of actual pain. Therefore, the progress d1 is identified and classified as psychogenic pain corresponding to (2) described above. Similarly, in a case where the measurement data of pain of past six times is in a situation of a progress d2 indicated by a dashed line in FIG. 9, a decrease of the value of the VAS in the vertical axis which is regarded as subjective is larger compared with a decrease of the measurement value of pain in the horizontal axis which is regarded as objective data. Based on the above, it is understood that decrease of actual pain is smaller in comparison with decrease of the pain felt by the subject 2. Therefore, the progress d2 is also classified as the psychogenic pain corresponding to (2) described above. Further, if the measurement data of pain of past six times is in a situation as a progress d3 indicated by a broken line in FIG. 9, a decrease of the pain measurement value in the horizontal axis and a decrease of the value of the VAS in the vertical axis are almost equal. Based on the above, it can be judged that a psychological factor is comparatively small, and thus the progress d3 is classified as the nociceptive pain corresponding to (1) described above. Other than the above, in a case where both pain measurement value and value of the VAS do not decrease along with lapse of time and indicate continuation of chronic pain, illustration thereof being omitted, such a progress is classified as neuropathic pain corresponding to (3) above.

Note that the minimum perception current value, the pain equivalent current value, the pain index, the VAS, and the pain measurement value are displayed for example in the display unit 6a, as shown in FIG. 3. In other words, the minimum perception current value, the pain equivalent current value, and the pain index are displayed in a measurement data display region α1 and a measurement result display region α2 in the display unit 6a. The VAS and the pain measurement value are displayed in measurement data display regions a2 and a7 in the display unit 6a. Other than the above, in the display unit 6a, the face scale is displayed in a measurement data display region α6a and the VAS is displayed in a measurement data display region α6b. For example, as a result that the subject points to a position corresponding to pain in the face scale displayed in the measurement data display region α6a, the value of the VAS displayed in the measurement data display region α6b can be determined.

In a display example shown in FIG. 3, in the measurement data display region α1, measurement values of three-time measurement of the minimum perception current values and an average value thereof are displayed below display of "Minimum". Besides, in the measurement data display region α1, measurement values (only one time of measurement is carried out in the display example of FIG. 3) of three-time measurement of the pain equivalent current values and an average value thereof are displayed below display of "Pain". Further, in the measurement data display region α1, the pain index is displayed on the right of display of "Pain Ratio". The pain index displayed in the measurement data display region α1 is a value obtained by dividing the average value of the pain equivalent current values by the average value of the minimum perception currents. Further, on the right of display of the pain equivalent current value, the average value of the minimum perception currents and the average value of the pain equivalent currents are displayed by means of a stacked column chart. In FIG. 3, a portion indicated by black color is the average value of the minimum perception currents and a portion indicated by white color is the average value of the pain equivalent currents.

Further, in the display example shown in FIG. 3, in the measurement result display region α2, measurement results of pain of six subjects 2 are displayed. Concretely, in the measurement result display region α2, an average value of minimum perception current values of each of the subjects 2 is displayed below display of "Min Ave", and an average value of pain equivalent current values of each of the subjects 2 is displayed below display of "Pain Ave". Further, the pain index of each of the subjects 2 is displayed below display of "Pain Ratio", and the average value of the minimum perception currents and the average value of the pain equivalent currents of each of the subjects 2 are displayed by means of a stacked horizontal bar chart in a left end. In FIG. 3, a portion indicated by black color is the average value of the minimum perception currents and a portion indicated by white color is the average value of the pain equivalent currents. Further, in the measurement result display region α2, a value of the VAS of each of the subjects 2 is displayed below display of "VAS". Further, a pain measurement value of each of the subjects 2 is displayed below display of "Pain Measurement Value". The above display may be measurement results of pain of past six-time measurement of one subject 2. Further, in a case of "Yes" in the step S8 of the flowchart in FIG. 7 such as a case where the value of the VAS and the pain measurement value in the measurement result display region α2 are measurement results of past six-time measurement of one subject 2, a classification result such as "nociceptive pain" is displayed beside display of "Classification" in a lower portion of the measurement result display region α2.

Note that in the display unit 6a, various information such as a gender and an age of the subject 2 is displayed in a subject data display region α3, types of graphs displayed in the measurement data display region α1 and the measurement result display region α2 are displayed in a graph type display region α4, and scales of the graphs displayed in the measurement data display region α1 and the measurement result display region α2 are displayed in a graph scale display region α5.

(Pain Given to Subject by Stimulation Current)

Figure 10B:
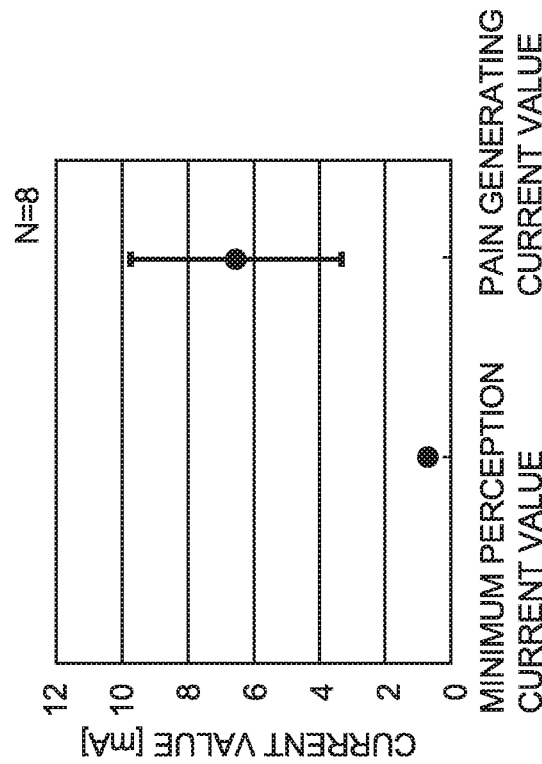
FIG. 10(A) and FIG. 10(B) are graphs showing measurement results of pain generating current values being current values of stimulation currents by which the subject feels pain and minimum perception current values.
Figure 10A:
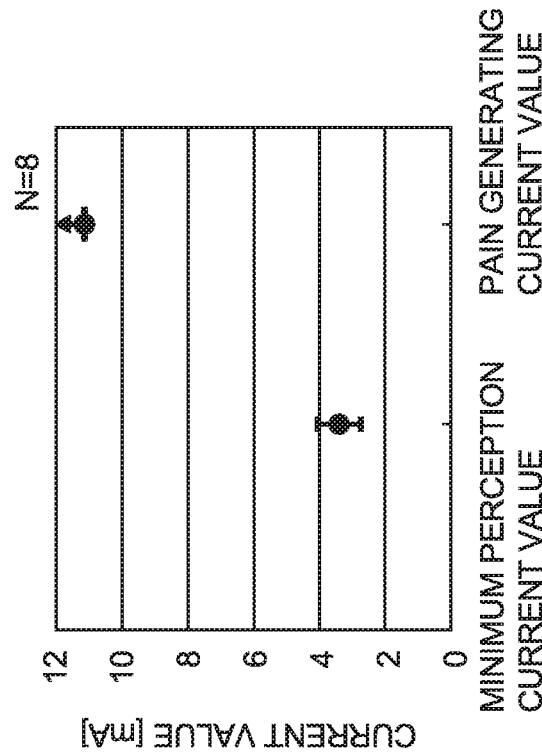

FIG. 10(A) and FIG. 10(B) are graphs showing measurement results of a pain generating current value being a current value of a stimulation current by which the subject 2 feels pain and the minimum perception current value, and FIG. 10(A) shows the measurement result at a time that the stimulation current according to the embodiment of the present invention is applied to the subject 2 while FIG. 10(B) shows the measurement result at a time that the stimulation current constituted by the conventional rectangular wave is applied to the subject 2.

When the stimulation currents of the present embodiment were applied to eight subjects 2, the minimum perception current value was 3.36±0.76 mA, as shown in FIG. 10(A). Further, the current values of the stimulation currents were increased to about 33 mA being an upper limit value of the pain measuring device 1, but the subjects 2 did not feel pain by the stimulation currents. Note that though not feeling pain by the stimulation currents, the subjects 2 felt a different kind of stimulation (that is, stimulation without pain) which is felt to have intensity nearly equal to that of pain, and thus quantitative evaluation of pain was possible based on largeness of this stimulation.

In contrast, when the stimulation currents constituted by the conventional rectangular waves were applied to the eight subjects 2, the minimum perception current value was 0.79±0.24 mA as shown in FIG. 10(B). Further, when the stimulation currents were increased, the subjects 2 felt pain by the stimulation currents. The pain generating current value being the current value of the stimulation current by which the subject 2 feels pain was 6.66±3.03 mA.

(Main Effect of the Present Embodiment)

In the pain measuring device 1 of the present embodiment, the stimulation currents in which the peak values of the power spectra change as indicated by the graphs G1, G2 of FIG. 4 are applied from the electrode 3a to the subject 2. Thus, as described by using FIG. 10(A), measurement of the pain felt by the subject 2 becomes possible without having the subject 2 feel new pain by the stimulation current. This measurement value is more objective compared with conventional one.

Figure 11:
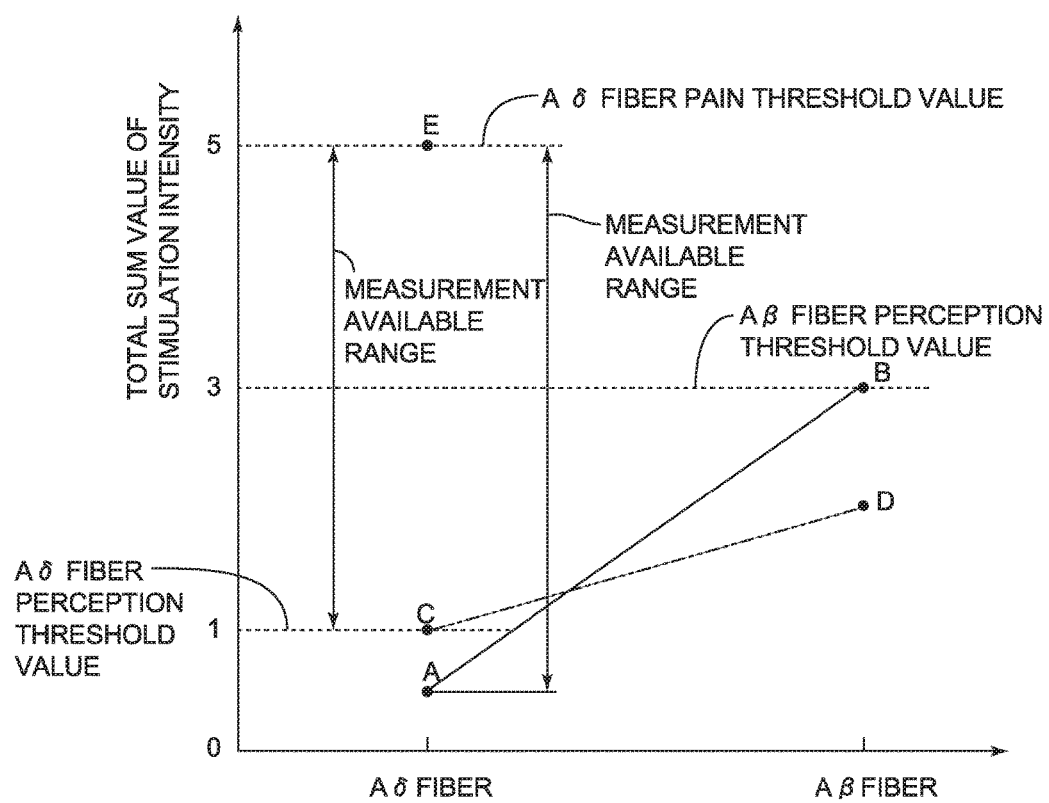
FIG. 11 is a typical graph for explaining intensity of stimulation which the stimulation current according to the embodiment of the present invention and the stimulation current constituted by the conventional rectangular wave each give to an Aδ fiber and an Aβ fiber.

The effect of the present embodiment will be described in more detail by using FIG. 11. FIG. 11 is a typical graph for explaining intensity of stimulation which the stimulation current according to the embodiment of the present invention and the stimulation current constituted by the conventional rectangular wave each give to the Aδ fiber and the Aβ fiber.

As described above, what is related to the stimulation to the Aδ fiber is considered to be the integration value of 50 Hz to 500 Hz of the power spectrum, and what is related to the stimulation to the Aβ fiber is considered to be the integration value of 50 Hz to 3000 Hz of the power spectrum. Therefore, here, the integration value of 50 Hz to 500 Hz of the power spectrum is defined as a total sum value of the stimulation intensity related to the stimulation to the Aδ fiber. Further, the integration value of 50 Hz to 3000 Hz of the peak values of the power spectrum is defined as a total sum value of the stimulation intensity related to the stimulation to the Aβ fiber.

Further, a minimum value (hereinafter, this value is referred to as an "Aδ fiber perception threshold value" and expressed so also in FIG. 11) which has the subjects 2 feel stimulation, being the total sum value of the Aδ fiber stimulation intensity, is known to be about one third of a minimum value (hereinafter, this value is referred to as an "Aβ fiber perception threshold value" and expressed so also in FIG. 11) which has the subject 2 feel stimulation, being the total sum value of the Aβ fiber stimulation intensity. Further, a minimum value (hereinafter, this value is referred to as an "Aδ fiber pain threshold value" and expressed so also in FIG. 11) which has the subjects 2 feel pain, being the total sum value of the Aδ fiber stimulation intensity, is known to be about five times the Aδ fiber perception threshold value. From the above, in FIG. 11, a vertical axis indicates the total sum value of the stimulation intensity, and a rate of the Aδ fiber perception threshold value, the Aβ fiber perception threshold value, and the Aδ fiber pain threshold value is indicated as values of the vertical axis. In the vertical axis in FIG. 11, since largeness of the Aδ fiber perception threshold value is "1", largeness of the Aβ fiber perception threshold value is "3", and the Aδ fiber pain threshold value is "5". Note that since the Aβ fiber is not related to transmission of pain, an Aβ pain threshold value is considered not to exist, theoretically.

When a proportion of the total sum value of the Aδ fiber stimulation intensity to the total sum value of the Aβ fiber stimulation intensity is calculated from the graph G1 or the graph G2 in FIG. 4 which indicates a characteristic of the stimulation current of the present embodiment, the proportion of the total sum value of the Aδ fiber stimulation intensity to the total sum value of the Aβ fiber stimulation intensity is about 1:6. On the other hand, when a proportion of the total sum value of the Aδ fiber stimulation intensity to the total sum value of the Aβ fiber stimulation intensity is calculated from the graph G3 or the graph G4 in FIG. 4 which indicates a characteristic of the conventional stimulation current, the proportion of the total sum value of the Aδ fiber stimulation intensity to the total sum value of the Aβ fiber stimulation intensity is about 1:2. Note that the proportion of the total sum value of the Aδ fiber stimulation intensity to the total sum value of the Aβ fiber stimulation intensity is equal to the proportion of the total sum value in the range of 50 Hz to 500 Hz of the peak values of the power spectrum related to the stimulation to the Aδ fiber and the total sum value in the range of 50 Hz to 3000 Hz of the peak values of the power spectrum related to the stimulation to the Aβ fiber.

Based on the proportion of the total sum value of the Aδ fiber stimulation intensity to the total sum value of the Aβ fiber stimulation intensity, and the measurement results (measurement results shown in FIGS. 10(A), 10(B)) of pain which the aforementioned stimulation currents give to the subject 2, in a case where the stimulation current of the present embodiment is used, since the proportion of the total sum value of the Aδ fiber stimulation intensity to the total sum value of the Aβ fiber stimulation intensity is always 1:6 even if the stimulation current is made larger, it is considered that the Aβ fiber first perceives the electric stimulation (that is, the Aβ fiber is related in measuring the minimum perception current value). On the other hand, in a case where the conventional stimulation current is used, since the proportion of the total sum value of the Aδ fiber stimulation intensity to the total sum value of the Aβ fiber stimulation intensity is always 1:2 even if the stimulation current is made larger, it is considered that the Aδ fiber first perceives the electric stimulation (that is, the Aδ fiber is related in measuring the minimum perception current value).

In other words, in a case where the stimulation current of the present embodiment is used, when the current value of the stimulation current is gradually increased from 0, the total sum value of the Aβ fiber stimulation intensity reaches the Aβ fiber perception threshold value before the total sum value of the Aδ fiber stimulation intensity reaches the Aδ fiber perception threshold value. In other words, the stimulation current of the present embodiment stimulates the Aβ fiber before the Aδ fiber. Further, since the proportion of the total sum value of the Aδ fiber stimulation intensity to the total sum value of the Aβ fiber stimulation intensity is about 1:6 in the stimulation current of the present embodiment, as shown in FIG. 11, when the total sum value of the Aβ fiber stimulation intensity reaches the Aβ fiber perception threshold value (that is, the total value of the Aβ fiber stimulation intensity is positioned at a point B), the total sum value of the Aδ fiber stimulation intensity is "0.5", which does not reach the Aδ fiber perception threshold value (that is, positioned at a point A).

Meanwhile, in a case where the conventional stimulation current is used, when the current value of the stimulation current is gradually increased from 0, the total sum value of the Aδ fiber stimulation intensity reaches the Aδ fiber perception threshold value before the total sum value of the Aβ fiber stimulation intensity reaches the Aβ fiber perception threshold value. Further, since the proportion of the total sum value of the Aδ fiber stimulation intensity to the total sum value of the Aβ fiber stimulation intensity is about 1:2 in the conventional stimulation current, as shown in FIG. 11, when the total sum value of the Aδ fiber stimulation intensity reaches the Aδ fiber perception threshold value (that is, the total sum value of the Aδ fiber stimulation intensity is positioned at a point C), the total sum value of the Aβ fiber stimulation intensity is "2", which does not reach the Aβ fiber perception threshold value (that is, positioned at a point D).

Note that though the point A and the point B are connected by a solid line and the point C and the point D are connected by a two-dot chain line in FIG. 11, these straight lines are drawn for the sake of convenience of easy viewability of the graphs and these straight lines do not have particular meanings.

A case where the current value of the stimulation current is further increased is considered. When the stimulation current is increased, the total sum value of the stimulation intensity rises. Then, when the total sum value of the Aδ fiber stimulation intensity reaches the Aδ fiber pain threshold value, the subject 2 feels new pain by the stimulation current. Thus, applying the stimulation current of the current value equal to or more than the Aδ fiber pain threshold value is cruel to the subject 2, and measurement of pain cannot be continued after the subject 2 begins to feel new pain by the stimulation current. In other words, measurement of pain by the pain measuring device 1 is possible from a time when the subject 2 begins to feel electric stimulation until the subject 2 feels pain by the electric stimulation. In other words, a range until the total sum value of the Aδ fiber stimulation intensity reaches the point E (until the total sum of the stimulation intensity becomes "5") is a measurement available range of pain of the subject 2 by the stimulation current without pain.

In the case where the stimulation current of the present embodiment is used, the minimum perception current value is a value of the stimulation current at a time that the Aβ fiber first perceives the electric stimulation, that is, at a time that the total sum value of the Aβ fiber stimulation intensity reaches the point B. At this time, the total sum value of the Aδ fiber stimulation intensity is 0.5 as described above and positioned at the point A, and thus if the total sum value of the Aδ fiber stimulation intensity is in a range of the point A to the point E, measurement of pain by the stimulation current without pain becomes possible. In other words, if the total sum value of the Aδ fiber stimulation intensity is in a range of 0.5 to 5, measurement of pain is possible, and it becomes possible to apply a stimulation current of a value of 10 times the minimum perception current value to the subject 2 as the stimulation current without pain. Note that a range of the total sum value of the Aβ fiber stimulation intensity corresponding to this pain measurement available range is 3 to 30.

In contrast, in the case where the conventional stimulation current is used, the minimum perception current value is a value of the stimulation current at a time that the Aδ fiber first perceives the electric stimulation, that is, at a time that the total sum value of the Aδ fiber stimulation intensity reaches the point C. Thus, if the total sum value of the Aδ fiber stimulation intensity is in a range of the point C to the point E, measurement of pain by the stimulation current without pain becomes possible. In other words, only at the time that the total sum value of the Aδ fiber stimulation intensity is in the range of 1 to 5, measurement of pain is possible, and only a stimulation current of a value of 5 times the minimum perception current value can be applied to the subject 2 as the stimulation current without pain. Note that a range of the total sum value of the Aβ fiber stimulation intensity corresponding to the pain measurement available range is 2 to 10.

As described above, in the case where the conventional stimulation current is used, only the stimulation current with the current value of five times the minimum perception current value can be applied to the subject 2, but, in contrast, in the case where the stimulation current of the present embodiment is used, the stimulation current with the current value of 10 times the minimum perception current value can be applied to the subject 2 without giving pain. In other words, in the case where the stimulation current of the present embodiment is used, a range where pain of the subject 2 can be measured by the simulation current without pain is two times that in the case where the conventional stimulation current is used, and it becomes possible to measure a degree of pain felt by the subject 2 in a broad range. Further, in the case where the stimulation current of the present embodiment is used, since the degree of pain can be measured in the broad range by the stimulation current without pain, as described by using FIG. 10(A), the subject 2 does not feel pain by the stimulation current even if the current value of the stimulation current is increased to about 33 mA being the upper limit value of the pain measuring device 1. In other words, it is possible to finish quantitative evaluation of pain of the subject 2 by the different kind of stimulation (that is, stimulation without pain) which is felt to have intensity nearly equal to that of pain, before the total sum value of the Aδ fiber stimulation intensity reaches the Aδ fiber pain threshold value, so that the subject 2 does not feel new pain by the stimulation current.

As described above, in the case where the stimulation current of the present embodiment is used, the proportion of the total sum value of the Aδ fiber stimulation intensity to the total sum value of the Aβ fiber stimulation intensity, that is, the proportion of the total sum value in the range of 50 Hz to 500 Hz of the peak values of the power spectrum related to the stimulation to the Aδ fiber to the total sum value in the range of 50 Hz to 3000 Hz of the peak values of the power spectrum related to the stimulation to the Aβ fiber, is about 1:6, and when the current value of the stimulation current is gradually increased from 0, the stimulation current stimulates the Aβ fiber earlier than the Aδ fiber. Thus, it becomes possible to measure the degree of the pain felt by the subject 2 in the broad range by the electric stimulation without pain.

Further, the stimulation current of the present embodiment contains a 250 Hz frequency component which stimulates the Aδ fiber efficiently and a 2000 Hz frequency component which stimulates the Aβ fiber efficiently. Thus, it becomes possible to measure pain by the different kind of electric stimulation with a sensation closer to the pain felt by the subject 2. In other words, if the stimulation current which does not contain the 250 Hz frequency component which efficiently stimulates the Aδ fiber related to transmission of pain is applied to the subject 2, it becomes possible to apply the different kind of electric stimulation without pain to the subject 2 in the broader range. However, if the 250 Hz frequency component which efficiently stimulates the Aδ fiber related to transmission of pain is not contained at all, the stimulation with a sensation completely different from pain is compared with the actual pain felt by the subject 2, and proper evaluation of pain is difficult. In contrast, as in the present embodiment, if the 250 Hz frequency component and the 2000 Hz frequency component are contained in the stimulation current, it becomes possible to measure pain by the different kind of electric stimulation with the sensation closer to the pain felt by the subject 2.

Note that in the pain measuring device 1 of the present embodiment, the stimulation current does not contain a 5 Hz frequency component which stimulates a C fiber related to transmission of continuous dull pain. Therefore, by this measuring apparatus, the subject does not feel continuous dull pain due to stimulation of the C fiber.

Further, in the stimulation current of the present embodiment, the peak values of the power spectrum are almost equal at least between 50 Hz to 500 Hz and are largest between 50 Hz and 2000 Hz. Therefore, generation of a waveform of the simulation current is easy.

Further, by using a relationship between the VAS or the face scale and the pain measurement value as in the present embodiment, the following becomes possible. That is, by making individual measurement results of pain of the pain measuring devices 1 correspond to common values of the VAS, it becomes possible to carry out comparison of the measurement results of pain among a plurality of subjects 2. Further, by analyzing a correspondence between the measurement result of the actual pain of the subject 2 and the value of the VAS which the subject 2 selects, it is possible to classify factors of pain or to identify a cause of pain, whereby diagnosis of a disease can be done.

Other Embodiments

Though the aforementioned embodiment is an example of a preferred embodiment of the present invention, the present invention is not limited thereto and can be modified in various ways within a range where the gist of the present invention is not altered.

Though the VAS or the face scale is used in the aforementioned embodiment, other subjective pain display means may be adopted. Further, it is possible to use a value expressing a pain equivalent current value by a common logarithm, a natural logarithm or the like, instead of the pain measurement value. That is, the above value may be used in an X axis in FIG. 9.

In the stimulation current of the aforementioned embodiment, the proportion of the total sum value of the Aδ fiber stimulation intensity to the total sum value of the Aβ fiber stimulation intensity is about 1:6. However, as is known from FIG. 11, if the proportion of the total sum value of the Aδ fiber stimulation intensity to the total sum value of the Aβ fiber stimulation intensity is equal to or more than 1:3, that is, if a value obtained by dividing the total sum value of the Aβ fiber stimulation intensity by the total sum value of the Aδ fiber stimulation intensity is equal to or more than 3, the Aβ fiber can be stimulated earlier than the Aδ fiber when the current value of the stimulation current is gradually increased from 0, so that it becomes possible to measure pain in a broader range compared with a conventional method.

Further, if the proportion of the total sum value of the Aδ fiber stimulation intensity to the total sum value of the Aβ fiber stimulation intensity becomes larger than 1:12, that is, if a value obtained by dividing the total sum value of the Aβ fiber stimulation intensity by the total sum value of the Aδ fiber stimulation intensity is larger than 12, stimulation to the Aβ fiber which is not related to transmission of pain becomes relatively large, so that it becomes difficult to measure pain by the different kind of electric stimulation with the sensation closer to pain felt by the subject 2. Thus, in order to measure pain by the different kind of electric stimulation with the sensation closer to pain, the proportion of the total sum value of the Aδ fiber stimulation intensity to the total sum value of the Aβ fiber stimulation intensity is preferable to be equal to or less than 1:12.

As described above, by making the proportion of the total sum value of the Aδ fiber stimulation intensity to the total sum value of the Aβ fiber stimulation intensity be in a range of 1:3 to 1:12, it becomes possible to measure the degree of pain felt by the subject 2 in the broad range by the electric stimulation without pain. Further, it becomes possible to measure pain by the different kind of electric stimulation which does not give pain and gives the sensation closer to the pain felt by the subject 2.

Further, transition of peak value of the power spectrum of the stimulation current having the aforementioned effect is not limited to the graph G1 or the graph G2 shown in FIG. 4. When the current value of the stimulation current is increased gradually from 0, if a condition that the Aβ fiber is stimulated earlier than the Aδ fiber or that the proportion of the total sum value of the Aδ fiber stimulation intensity to the total sum value of the Aβ fiber stimulation intensity within the range of 1:3 to 1:12 is satisfied, the peak value of the power spectrum of the stimulation current may change as in a graph G3 shown in FIG. 12(A) or in a graph G4 shown in FIG. 12(B).

Figure 12A:
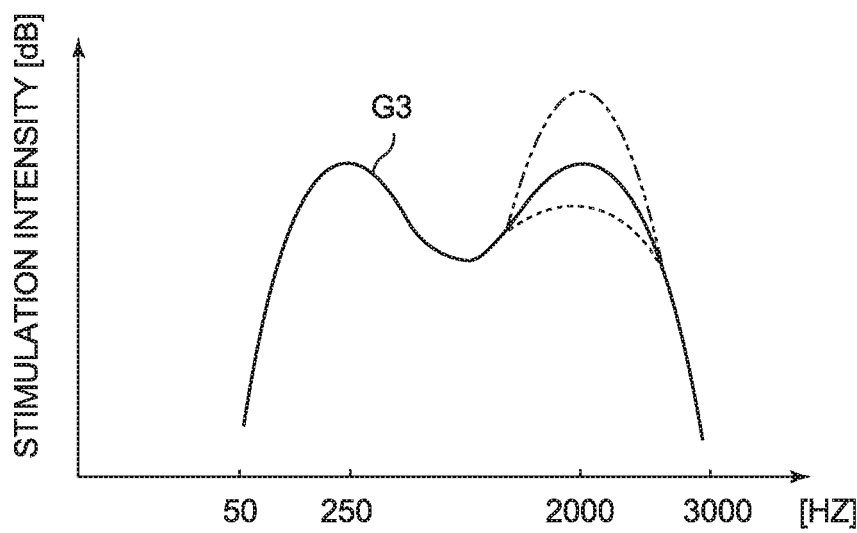
FIG. 12(A) and FIG. 12 (B) are graphs showing peak values of power spectra of stimulation currents according to other embodiments of the present invention.

In other words, as shown in FIG. 12(A), the peak value of the power spectrum may change in a manner that a maximum value of a curved line connecting the peak values of the power spectrum appears in a neighborhood of 250 Hz and in a neighborhood of 2000 Hz. In this case, the peak value of the power spectrum may change in a manner that the maximum values in the neighborhood of 250 Hz and in the neighborhood of 2000 Hz are equal and these maximum values become the largest values of the peak values of the power spectrum as indicated by a solid line in FIG. 12(A), and the maximum value in the neighborhood of 250 Hz may be the largest value of the peak values of the power spectrum as indicated by a broken line in FIG. 12(A). Further, the maximum value in the neighborhood of 2000 Hz may become the largest value of the peak values of the power spectrum as indicated by a two-dot chain line in FIG. 12(A).

Figure 12B:
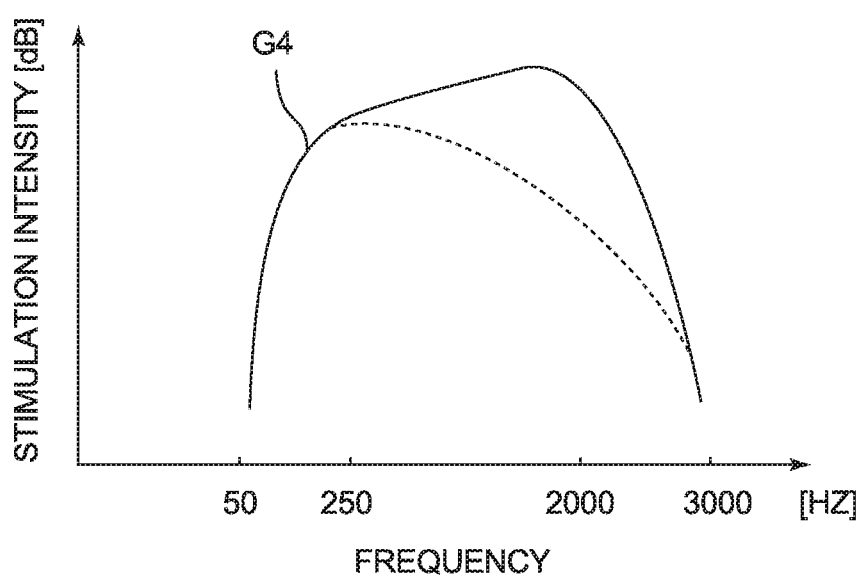

Further, the peak value of the power spectrum may change to increase gradually from the neighborhood of 250 Hz toward the neighborhood of 2000 Hz and thereafter to decrease gradually as indicated by a solid line in FIG. 12(B), and the peak value of the power spectrum may change to decrease gradually from the neighborhood of 250 Hz as a frequency becomes larger, as indicated by a broken line in FIG. 12(B).

Note that as shown in FIG. 12(A) and FIG. 12(B), the stimulation current is preferable to have only frequency components within a range of 50 Hz to 3000 Hz. A frequency component of equal to or less than 50 Hz and a frequency component of equal to or more than 3000 Hz are not related to stimulation to the Aδ fiber and the Aβ fiber. Therefore, in a case where the stimulation current has only the frequency component within the range of 50 Hz to 3000 Hz, it is possible to stimulate the Aδ fiber and the Aβ fiber efficiently by a small stimulation current.

Further, in the aforementioned embodiment, the stimulation current contains the 250 Hz frequency component and the 2000 Hz frequency component. In addition to the above, it is possible to stimulate the Aδ fiber by getting the stimulation current not to contain the 250 Hz frequency component but to contain the frequency component in the neighborhood of 250 Hz. Similarly, it is possible to stimulate the Aβ fiber by getting the stimulation current not to contain the 2000 Hz frequency component but to contain the frequency component in the neighborhood of 2000 Hz.

Further, though the factors or causes of pain are classified into or identified as three of (1) nociceptive pain, (2) psychogenic pain, and (3) neuropathic pain, it is possible to classify into (1) nociceptive pain and others, to classify into (2) psychogenic pain and others, or to classify into three of (1) nociceptive pain, (3) neuropathic pain and others, that is, to classify into or identify as what includes any one or two or more of (1), (2) and (3) described above.

REFERENCE SIGNS LIST

1 . . . pain measuring device, 2 . . . subject, 3 . . . electrode band, 3a . . . electrode, 6 . . . PC (part of means to display), 9 . . . MPU (part of stimulation current generation means, part of means to display, means to compare, a means to classify), 10 . . . boosting transformer (part of stimulation current generation means), 11 . . . voltage control circuit (part of stimulation current generation means), 12 . . . output control circuit (part of stimulation current generation means), 13 . . . protection circuit (part of stimulation current generation means), 14 . . . current detection circuit (part of stimulation current generation means)

The invention claimed is:

1. A pain measuring device which includes an electrode to be attached to a subject and a main body unit having a stimulation current generator generating a stimulation current to be supplied to the electrode and which measures pain felt by the subject based on the stimulation current applied from the electrode to the subject, the pain measuring device comprising:

a display which displays a relationship between a pain measurement value of a value founded on the stimulation current and a value of a visual analogue scale (VAS) or a face scale determined by the subject, wherein the stimulation current contains a 250 Hz frequency component, a 2000 Hz frequency component, and a 5 Hz frequency component equal to or less than one thousandth of the 250 Hz or 2000 Hz frequency component;

a minimum perception current value is defined as a first current which the subject feels electric stimulation first when a current value of the stimulation current applied to the subject is gradually increased from 0, and a pain equivalent current value is defined as a second current which gives a sensation equal to a sensation of pain felt by the subject due to a disease when the current value of the stimulation current is further increased, a pain index is defined as pain index=pain equivalent current value/minimum perception current value, the value of the VAS or the face scale determined by the subject corresponds to the pain felt by the subject or the face scale corresponding to the pain felt by the subject, the main body unit is configured to classify a factor of pain by comparing a pain measurement value calculated from the pain index and the VAS or the face scale in chronological order, wherein the pain measurement value is a) a logarithmic value or b) a logarithmic-type value calculated by ((pain index−1)/pain index)×100, wherein the main body unit is configured to classify the factor of pain as psychogenic pain in a case when a decrease of the value of the VAS or the face scale is smaller compared with a decrease of the pain measurement value along with lapse of time, classify the factor of pain as psychogenic pain in a case when the decrease of the value of the VAS or the face scale is larger compared with the decrease of the pain measurement value along with lapse of time, classify the factor of pain as nociceptive pain in a case when the decrease of the value of the VAS or the face scale is equal to the decrease of the pain measurement value along with lapse of time, and classify the factor of pain as neuropathic pain in a case where both pain measurement value and value of the VAS or the face scale do not decrease along with lapse of time, wherein the display is configured to display the classified factor of pain.

2. The pain measuring device according to claim 1, wherein the pain measurement value is logarithmic value defined as one of the following:

pain measurement value=100×Log 10 (pain index).

\* \* \* \* \*